US011172683B2

(12) United States Patent
Buyondo et al.

(10) Patent No.: US 11,172,683 B2
(45) Date of Patent: Nov. 16, 2021

(54) SYNERGISTIC COMBINATIONS OF MONOCHLORAMINE AND ORGANIC ACID, AND METHODS OF USING THE SAME FOR MICROBIAL CONTROL

(71) Applicant: Buckman Laboratories International, Inc., Memphis, TN (US)

(72) Inventors: John P. Buyondo, Arlington, TN (US); Mark L. Reed, Cordova, TN (US); Bernard Janse, Collierville, TN (US)

(73) Assignee: BUCKMAN LABORATORIES INTERNATIONAL, INC., Memphis, TN (US)

( * ) Notice: Subject to any disclaimer, the term of this patent is extended or adjusted under 35 U.S.C. 154(b) by 111 days.

(21) Appl. No.: 16/254,631

(22) Filed: Jan. 23, 2019

(65) Prior Publication Data

US 2019/0230932 A1    Aug. 1, 2019

Related U.S. Application Data

(60) Provisional application No. 62/623,628, filed on Jan. 30, 2018.

(51) Int. Cl.
*A01N 59/00* (2006.01)
*C12P 7/06* (2006.01)
*A01N 37/36* (2006.01)
*A01N 33/14* (2006.01)

(52) U.S. Cl.
CPC ............. *A01N 59/00* (2013.01); *A01N 33/14* (2013.01); *A01N 37/36* (2013.01); *C12P 7/06* (2013.01)

(58) Field of Classification Search
CPC .............. A61K 2300/00; A61K 31/185; A61K 31/197; A61K 31/198; A61K 33/00; A61K 33/16; A61K 33/18; A61K 33/20; A61K 31/13; A61K 31/18; A61K 31/195; A61K 31/66; A61K 31/69; A61K 45/06; C02F 1/50; C02F 1/686; C02F 1/722; C02F 1/76; C02F 1/766; C02F 2103/28; C02F 2303/04; C02F 1/001; C02F 9/00; C02F 1/02; C02F 1/72; C02F 1/78; C02F 2103/42; C02F 1/32; C02F 2103/023; C02F 2103/16; C02F 2103/24; C02F 2103/32; D21C 9/008; D21H 21/04; D21H 21/36; A61P 31/00; A61P 31/04; A61P 31/10; A61P 31/12; A61P 17/02; A61P 17/00; A61P 17/06; A61P 1/02; A61P 27/02; A61P 31/02; C07C 309/14; C07C 239/04; Y02A 50/30; Y02A 50/473; A01N 59/00; A01N 63/50; A01N 37/16; A01N 33/14; A01N 37/36; A01N 2300/00; A01N 63/10; A01N 25/10; A01N 59/06; A01N 59/02; A01N 59/04; A01N 59/08; A01N 25/04; A01N 25/02; A01N 41/08; A01N 43/36; A01N 43/50; A01N 43/66; A23L 3/358; A23L 3/3508; A23L 3/349; C12P 7/06; A23B 7/157; A23B 9/26; A23B 9/30; A23B 4/12; A23B 4/20; A23B 7/10; A23B 7/154; B08B 17/02; C07K 7/06; C07K 7/08; C09D 5/14; C09D 5/1637; C09D 5/1693; Y02E 50/10; A23V 2002/00; A61Q 1/00; A61Q 5/006; B27K 2240/20; B27K 3/32; C12N 1/20; C12N 1/38; C01B 21/083; C01B 21/09; C01B 21/091
See application file for complete search history.

(56) References Cited

U.S. PATENT DOCUMENTS

| | | | | |
|---|---|---|---|---|
| 4,239,622 A * | 12/1980 | Ridgway | ............... | A01N 59/00 424/616 |
| 5,444,078 A | 8/1995 | Yu et al. | | |
| 5,637,587 A * | 6/1997 | Gross | ..................... | A01N 43/90 422/28 |
| 5,753,180 A * | 5/1998 | Burger | .................. | A01N 35/06 134/42 |
| 6,149,822 A * | 11/2000 | Fabri | ..................... | A01N 35/10 162/161 |

(Continued)

FOREIGN PATENT DOCUMENTS

| CN | 103451046 A | 12/2013 |
|---|---|---|
| SU | 424549 A1 | 4/1974 |

(Continued)

OTHER PUBLICATIONS

Silva et al., "Study of the Formatin of Stale High Concentrated Monochloramine Solutions", Enpromer, 2nd Mercousur Congress on Chem. Eng. 4th Mercousur Congress on Process Syst. Eng, 2003, pp. 1-9. (Year: 2003).*

(Continued)

*Primary Examiner* — Deborah K Ware
(74) *Attorney, Agent, or Firm* — Kilyk & Bowersox, P.L.L.C.

(57) ABSTRACT

Methods for controlling the growth of microorganisms in or on a product, material, or medium, such as a fermentable or fermenting medium, susceptible to attack by a microorganism, by treating with aqueous solution comprising monochloramine and at least one organic acid in a synergistically microbicidally effective combined amount to control unwanted microbial growth. Microbicidal aqueous solutions containing monochloramine and at least one organic acid in a synergistically microbicidally effective combined amount to control the growth of at least one microorganism are also described.

10 Claims, 3 Drawing Sheets

(56) References Cited

U.S. PATENT DOCUMENTS

| | | | | |
|---|---|---|---|---|
| 7,052,614 | B2* | 5/2006 | Barak | C02F 1/722 210/752 |
| 7,189,329 | B2* | 3/2007 | Barak | D21H 21/04 210/752 |
| 7,628,929 | B2* | 12/2009 | Barak | D21H 21/04 210/752 |
| 7,846,971 | B2* | 12/2010 | Najafi | A61P 31/10 514/612 |
| 7,893,109 | B2* | 2/2011 | Bassiri | A61P 17/00 514/612 |
| 7,927,496 | B2* | 4/2011 | Barak | C02F 1/766 210/752 |
| 8,168,072 | B2* | 5/2012 | Barak | D21H 21/04 210/752 |
| 8,444,858 | B2* | 5/2013 | Barak | C02F 1/766 210/696 |
| 8,633,134 | B2* | 1/2014 | Kaiser | C07D 261/04 504/100 |
| 8,951,960 | B2 | 2/2015 | Wiatr et al. | |
| 9,458,164 | B2* | 10/2016 | Finlay | A61K 31/5025 |
| 9,955,698 | B2 | 5/2018 | Oppong et al. | |
| 10,212,937 | B2 | 2/2019 | Oppong et al. | |
| 2003/0121868 | A1* | 7/2003 | Barak | C02F 1/50 210/764 |
| 2013/0029884 | A1* | 1/2013 | Malchesky | C09K 8/605 507/219 |
| 2014/0335203 | A1 | 11/2014 | Consalo et al. | |
| 2016/0016961 | A1* | 1/2016 | Finlay | A61P 25/28 514/248 |
| 2016/0058023 | A1 | 3/2016 | Mullen et al. | |
| 2017/0107543 | A1 | 4/2017 | Buyondo et al. | |
| 2017/0118990 | A1* | 5/2017 | Oppong | A23B 9/30 |

FOREIGN PATENT DOCUMENTS

| | | |
|---|---|---|
| WO | 2017074720 A1 | 5/2017 |
| WO | 2017075311 A1 | 5/2017 |

OTHER PUBLICATIONS

Taylor et al "Chlorine, Chloramine, Chlorine Dioxide, and Ozone Susceptibility of Mycobacterium avium", App. and Env. Microb. vol. 66, No. 4, pp. 1702-1705, Apr. 2000. (Year: 2000).*

WHO/SDE/WSH/03.04/83 Engl only, "Monochloramine in Drinking-water", Background Document for devel. of WHO Guidelines for Drinking-water Quality, World Health Organization, pp. 1-13, 2004. (Year: 2004).*

International Search Report and Written Opinion issued in corresponding International Patent Application No. PCT/US2019/014644 dated Apr. 3, 2019 (25 pages).

Carlson et al: "Characterization of the products from the reaction of hydroxybenzoic and hydroxycinnamic acids with aqueous solutions of chlorine, chlorine dioxide, and chloramine," Database Accession No. 1986:155562, 1986; Water Chlorination: Chem., Environ. Impact Health Eff., Proc. Conf., 5th, Meeting Date 1984, 835-41.

Schmitz et al., "Hydrierungen mit Ammoniak und Chlor", Angewandte Chemie, 1961, vol. 73, No. 24, p. 807.

Perez-Garcia et al., "Chloramine, a sneaky contaminant of dialysate", Nephrol Dial Transplant, 1999, pp. 2579-2582.

Gray et al., "Ch. 16: Chloramine Equilibria and the Kinetics of Disproportionation in Aqueous Solution" In "Organometals and Organometalloids: Occurence and Fate in the Environment", American Chemical Society, 1979, vol. 82, pp. 264-277.

Huang, "Reactions between Aqueous Chlorine and Ammonia: A Predictive Model", Northeastern University, Boston, MA. U.S.A., Dissertation, 2008, pp. 1-171, https://repository.library.northeastern.edu/files/neu:817/fulltext.pdf.

Valentine et al., "General Acid Catalysis of Monochloramine Disproportionation", Environmental Science & Technology, 1988, vol. 22, No. 6, pp. 691-696.

Victorin et al., "Redox potential measurements for determining the disinfecting power of chlorinated water", The Journal of Hygiene, 1972, vol. 70, No. 2, pp. 313-323.

Vikesland et al., "Monochloramine Decay in Model and Distribution System Waters", Water Research, 2001, vol. 35, No. 7, pp. 1766-1776.

* cited by examiner

SYNERGISTIC COMBINATIONS OF MONOCHLORAMINE AND ORGANIC ACID, AND METHODS OF USING THE SAME FOR MICROBIAL CONTROL

This application claims the benefit under 35 U.S.C. § 119(e) of prior U.S. Provisional Patent Application No. 62/623,628, filed Jan. 30, 2018, which is incorporated in its entirety by reference herein.

BACKGROUND OF THE INVENTION

The present invention relates to synergistic combinations of antimicrobials in aqueous solutions or formulations and methods of their use for controlling the growth of microorganisms on a variety of mediums, substrates, and in liquid systems, such as ethanol fermentation systems. More particularly, the present invention relates to using monochloramine and organic acid, such as citric acid, in aqueous treatment solutions and/or for treatment of aqueous systems.

Many industrial materials and media when wet or subjected to treatment in water are susceptible to bacterial, fungal, and/or algal deterioration or degradation. A large variety of commercial, industrial, agricultural, and wood materials or products are subject to microbiological attack or degradation which reduces or destroys their economic value. These industrial materials and media include, but are not limited to, for example, wood pulp, wood chips, lumber, adhesives, coatings, animal hides, paper mill liquors, pharmaceutical formulations, cosmetic formulations, toiletry formulations, geological drilling lubricants, petrochemicals, agrochemical compositions, paints, leathers, plastics, seeds, plants, wood, metalworking fluids, cooling water, recreational water, influent plant water, waste water, pasteurizers, retort cookers, tanning liquors or solutions, starch, proteinaceous materials, acrylic latex paint emulsions, and textiles. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

To control deterioration or degradation caused by microorganisms, various industrial microbicides are used. Workers in the trade have continued to seek improved biocides that have low toxicity, are cost effective, and/or are also capable of exhibiting a prolonged biocidal effect against a wide variety of microorganisms with regular use.

Aqueous systems are also highly subject to microbiological growth, attack, and degradation. These aqueous systems may be fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiological growth and thus attack and degradation.

Microbiological degradation of aqueous systems may manifest itself as a variety of problems, such as loss of viscosity, gas formation, objectionable odors, decreased pH, emulsion breaking, color change, and/or gelling. Additionally, microbiological deterioration of aqueous systems can cause fouling of the related water-handling system, which may include cooling towers, pumps, heat exchangers, pipelines, heating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and/or yeast-like organisms. Slime reduces yields in production and causes plugging, bulking, and other problems in industrial water systems.

Some industrial production processes involving fermentation, such as ethanol production processes, need microbial growth control. In these process environments, it is desirable to control unwanted microbes that can contaminate these processes without harming beneficial microbes present or used in the system.

In ethanol production, ethanol can be produced by fermentation using a wide variety of starch containing raw materials. Starch-based ethanol production generally includes preparing a mass of starchy feedstock that contains or can be degraded into fermentable sugars, adding water to make a mash, enzymatic liquefaction/saccharification of carbohydrates into fermentable sugars, and adding yeast which ferments the sugar into ethanol and carbon dioxide. Ethanol is recovered by subjecting the fermented mash to distillation. A co-product of distillation in ethanol production is non-starchy solids containing proteins, fibers, and oils, which may be processed to produce "distillers dried grains with solubles" or "DDGS". DDGS are nutrient-rich and are commercially sold as an animal feed, feed supplement, or plant fertilizer.

A problem in the ethanol production industry is that the ethanol fermentation system can become contaminated with bacteria that reduce production yields. This contamination can occur in one or more vessels used in holding, propagation and fermentation, including pre-fermentation holding tanks, propagation tanks, fermentations tanks, and piping and process equipment between these units. "Lactic acid bacteria" is one class of bacteria that poses a problem in this respect. Lactic acid bacteria include, for example, *Lactobacillus, Pediococcus, Leuconostoc* and *Weissella* species. Acetic acid bacteria, e.g., *Acetobacter* sp., can also cause problems by producing acetic acid, lactic acid, or other organic acids which foul the process and reduce the yields of ethanol. Yeast converts sugars to ethanol, but bacteria also convert those same sugars to make lactic or acetic acid instead of ethanol, leading to reductions in ethanol production yield. To control the outbreak of such bacteria, antibiotics, for example, virginiamycin, penicillin, erythromycin, and tylosin, have been used in ethanol fermentation processes. The risk of the bacteria developing drug-resistance to antibiotics from their use or overuse is a concern. Further, questions have been raised about non-specificity of the antibiotic to the target bacteria and fermentation products. Concerns also have been raised about the presence of antibiotic residues in the DDGS destined for animal feeds. Alternatives to antibiotics are needed for ethanol fermentation processes.

Oxidizing based chemistries proposed for fermentation systems that are based on usage of a single type of microbiocide do not significantly reduce and/or control bacteria growth, or would require significantly high concentration of a microbiocide to control bacterial growth, or are nonselective in anti-microbial action. Chlorine dioxide (i.e., $ClO_2$), for example, has been proposed as an oxidizing biocide. However, chlorine dioxide is a strong oxidizing agent which has nonselective antimicrobial action. Chlorine dioxide attacks both unwanted bacteria and yeast crucial to the fermentation process. Loss of yeast translates into loss of ethanol yield and/or a "sluggish" fermentation and/or a "stuck" fermentation. Chloride dioxide also generates chloride ions, which can corrode equipment and lead to iron deposits or pitting in the process equipment, as well as release iron and chromium into the process system, which can require costly repairs.

Despite the existence of microbicides, the industry is constantly seeking more cost-effective technology which offers equal or better protection at lower cost and/or lower concentration. The concentration of conventional microbicides and the corresponding treatment costs for such use, can be relatively high. Important factors in the search for cost-effective microbicides include the duration of microbicidal effect, the ease of use, the effectiveness of the microbicide per unit weight, and the ability to displace antibiotics for bacterial control with minimal adverse system or environmental impact of their own.

SUMMARY OF THE INVENTION

It is a feature of this invention to provide a combination of microbiocides in an aqueous solution capable of synergistically controlling the growth of at least one microorganism, for example, fungi, bacteria, algae, or mixtures thereof, for example, over short or over prolonged periods of time. Methods of controlling the growth of at least one microorganism in or on a product, material, or medium with or in an aqueous solution containing the combination of microbiocides are also features of this invention.

Methods and aqueous solutions for preventing damage during storage or loss of yield in an industrial process caused by undesirable microorganisms, such as undesirable bacteria, fungi, algae, or mixtures thereof, are described.

The present invention, in part, relates to a method of controlling the growth of at least one microorganism in or on a product, material, or medium susceptible to attack by a microorganism. The method includes the step of treating the product, material or medium with aqueous solution comprising (a) monochloramine and (b) at least one organic acid, wherein components (a) and (b) are present in a synergistically microbicidally effective combined amount to control the growth of at least one microorganism.

The present invention further provides a method to control growth of at least one contaminant microorganism in a fermentable carbohydrate-containing feedstock. This method includes the step of contacting the fermentable carbohydrate-containing feedstock with (a) monochloramine and (b) at least one organic acid, wherein components (a) and (b) are present in a synergistically microbicidally effective combined amount to control the growth of at least one contaminant microorganism in the fermentable carbohydrate-containing feedstock.

The present invention, in addition, provides a method for producing ethanol by fermentation with controlled growth of contaminant microorganisms. This method includes the steps of a) adding (a) monochloramine and (b) at least one organic acid to fermentable carbohydrate-containing feedstock to provide treated feedstock, wherein components (a) and (b) are present in a synergistically microbicidally effective combined amount to control the growth of at least one contaminant microorganism in the treated feedstock, b) fermenting the treated feedstock in the presence of yeast in a vessel to produce fermented mash comprising ethanol and a solids content, and c) distilling the fermented mash to separate at least a portion of the ethanol from stillage comprising the solids content.

The present invention also provides an aqueous solution or formulation comprising a) monochloramine and b) at least one organic acid, where components a) and b) are present in a combined amount synergistically effective to control the growth of at least one microorganism.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

It is understood that both the foregoing general description and the following detailed description are exemplary and explanatory only, and are not restrictive of the present invention as claimed.

The accompanying drawings, which are incorporated in and constitute a part of this application, illustrate some of the features of the present invention and together with the description, serve to explain the principles of the present invention.

DETAILED DESCRIPTION

Figure 1:
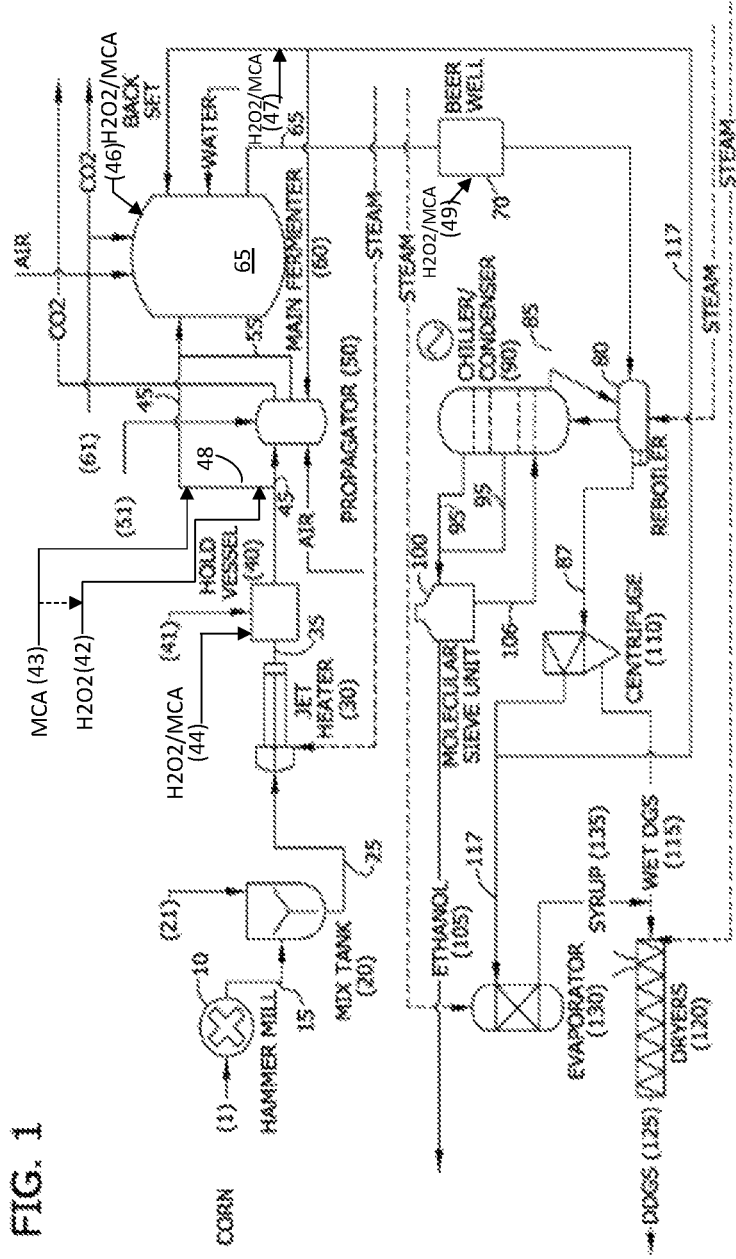
FIG. 1 illustrates a process flow diagram of a method of treating an ethanol fermentation system with a combination of monochloramine and organic acid to provide synergistic microbicidal control according to an embodiment of the present invention.

The present invention provides a method to control the growth of one or more microorganisms in or on a product, material, or medium susceptible to attack or contamination by a microorganism by treatment with an aqueous solution comprising a combination or mixture (or a formulation) of a) monochloramine and b) at least one organic acid, such as citric acid or other organic acid. The monochloramine and organic acid can be preferably present in a combined amount synergistically effective to control the growth of at least one microorganism. Synergistic combinations of these microbiocides used in methods and formulations of the present invention can deliver an antimicrobial effect greater than the sum of the individual microbiocides, and thus can provide an improved performance as compared to combinations which are merely additive in terms of antimicrobial efficiency. The microbicidally or synergistically effective amount can vary in accordance with the material or medium to be treated and can, for a particular application, be routinely determined by one skilled in the art in view of this disclosure. The combined use of a) monochloramine and b) at least one organic acid can provide superior microbicidal activity at low concentrations or other concentrations against a wide range of microorganisms. The terms "microbiocide" or "biocide" as used herein, can refer to a chemical substance capable of controlling bacteria in a selective way.

The present invention can be used to provide growth control of at least one contaminant microorganism in any environment where monochloramine is used. The present invention can be used to control microbial growth in higher organic load environments, such as where fermentable carbohydrate-containing feedstock are present in industrial ethanol fermentation processes, pharmaceutical processes, or other fermentation-involved processes. These methods can include a step of contacting fermentable carbohydrate-containing feedstock with (a) monochloramine and (b) at least one organic acid present in a synergistically microbicidally effective combined amount to control the growth of at least one contaminant microorganism in the fermentable carbohydrate-containing feedstock. Though not desiring to be bound to any theory, the organic acid may act as a scavenger to allow monochloramine to have a greater impact per unit time without adversely impacting yeast health in fermentation processes. As other advantages, the combined use of monochloramine and organic acid in an ethanol fermentation process can provide elimination or reduction in antibiotics in fermentation, reduction in lactic acid and acetic acid production in fermentation, increased yeast cell growth, viability, budding and vitality in fermentation, increased ethanol production in corn ethanol production, improved plant runnability, reduced production cost, increased value of dried distiller's grains for animal feed in corn ethanol production, and/or other improvements, or any combinations of these improvements.

The present invention provides an aqueous solution or formulation, which can be used in methods of this invention, which has a) monochloramine and b) at least one organic acid present in a combined amount synergistically effective to control the growth of at least one microorganism. The term "aqueous solution" as used herein can, as an example, refer to a solution that is predominantly water (e.g., over 50% by volume water such as over 75% by volume, over 95% by volume, or over 99% by volume water) and retains the solution characteristics of water. Where the aqueous solution contains solvents in addition to water, water is typically the predominant solvent.

The pH of the aqueous solution can be from about 4 to about 12, such as from about 4 to about 11, or from about 4 to about 10, or from about 4 to about 9, or from about 4 to about 8, or from about 4 to about 7, or from about 4 to about 6, or from about 5 to about 11, or from about 7 to about 10, or from 7.1 to 12, or from 7.5 to 10, or from 8 to 10. The aqueous solution can further include least one pH control agent, such as at least one acid or at least one base, or the aqueous solution may not include a pH control agent. If a pH control agent is included, the aqueous solution can include at least one acid, such as sulfuric acid and/or other acid, or at least one base, such as sodium hydroxide and/or other base. The addition or presence of at least one base along with the monochloramine and organic acid in the aqueous solution can provide optimal control of pathogenic bacteria. Some industrial processes involve lower pH conditions in an aqueous system during at least part of the process, such as ethanol fermentation processes, which can perform fermentation at a lower pH (e.g., about 4 to about 5.5). Fermentable carbohydrate-containing feedstock which can be used for ethanol fermentation can have a pH of from about 4 to about 12, or from about 4 to about 7. Before reaching the fermentation vessel, the fermentable carbohydrate-containing feedstock can be treated with an aqueous solution that combines the monochloramine and organic acid in a synergistically effective combined amount (and optionally with at least one base or pH control agent) to control the growth of at least one unwanted microorganism in the feedstock. This pre-fermentation treatment can be performed, with or without pH adjustment, on the fermentable carbohydrate-containing feedstock in piping, in process units or equipment, or in combinations of these, upstream (in advance) of the vessel(s) in which fermentation is performed (e.g., before where fermentation yeast and nutrients are introduced and combined with the fermentable carbohydrate-containing feedstock).

In lieu of adding the aqueous solution of the present invention to a material or medium to be treated, the monochloramine and organic acid, such as citric acid, and, if used, at least one base, can be separately added to the product, material, or medium to be treated, such as indicated for ethanol fermentation processes. If separately added, these components are individually added so that the final amount of the mixture of monochloramine and organic acid at the time of use can preferably be that amount synergistically effective to control the growth of at least one microorganism in the treated product, material, or medium. In an ethanol fermentation process, the organic acid and monochloramine can be added separately to fermentable carbohydrate-containing feedstock or other process fluid in a holding vessel, or separately in piping, or separately in both of these process equipment or other process units or equipment, located in advance of the fermentation vessel. Alternatively or in addition, the organic acid and monochloramine can be added directly into the fermentation vessel, or after the fermentation vessel, or any combinations of these different introduction points.

The combined use of a) monochloramine and b) at least one organic acid in an aqueous solution is useful in preserving various type of products, media, or materials susceptible to attack by at least one microorganism. In the present invention, aqueous solutions comprising a) monochloramine and b) at least one organic acid (and optionally at least one base or pH control agent) are useful in preserving or controlling the growth of at least one microorganism in various types of industrial and/or food products, media, or materials susceptible to attack by microorganisms. The material or medium can be in the form of a solid, a dispersion, an emulsion, a mash, a slurry, or a solution. Such media or materials include, but are not limited to, for example, fermentation media/materials (as indicated), dyes, pastes, lumber, leathers, textiles, pulp, wood chips, tanning liquor, paper mill liquor, fiberglass, dairy processing, poultry processing, meat processing (e.g., beef, pork, lamb, or chicken), meat packing plant, animal slaughter houses, polymer emulsions, paints, paper and other coating and sizing agents, metalworking fluids, geological drilling lubricants, petrochemicals, cooling water systems, recreational water, influent plant water, waste water, pasteurizers, retort cookers, pharmaceutical formulations, cosmetic formulations, and toiletry formulations.

The combined use of a) monochloramine and b) at least one organic acid (and optionally the at least one base or pH control agent) in aqueous solutions can also be used to treat or preserve materials and media that include, but are not limited to, for example, fermentable carbohydrate-containing mashes or solutions (as indicated), wood pulp, wood chips, lumber, adhesives, coatings, animal hides, paper mill liquors, pharmaceutical formulations, cosmetic formulations, toiletry formulations, geological drilling lubricants, petrochemicals, agrochemical compositions, paints, leathers, plastics, seeds, plants, wood, metalworking fluids, cooling water, recreational water, influent plant water, waste water, pasteurizers, retort cookers, tanning liquors or solutions, starch, proteinaceous materials, acrylic latex paint emulsions, and textiles.

The combined use of a) monochloramine and b) at least one organic acid (and optionally at least one base or pH control agent) in aqueous solutions can be used to treat or preserve aqueous systems, such as ones subject to microbiological growth, attack, and degradation. These aqueous systems may be or include, but are not limited to, fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. Additionally, with the present invention, microbiological deterioration of aqueous systems can be prevented or controlled including, but not limited to, related water-handling system, which may include cooling towers, pumps, heat exchangers, and pipelines, heating systems, scrubbing systems, and other similar systems, and the like.

The combined use of a) monochloramine and b) at least one organic acid (and optionally the at least one base or pH control agent) in aqueous solutions can also be used to protect or treat or preserve foods and/or surfaces in contact with food, such as fresh foods (e.g., vegetables and fruits) or meats, or dairy products or processing, for instance, to extend shelf life. The present invention can be used to protect or treat facilities that process food (meats, fruits, vegetables) including but not limited to the surfaces and machinery and devices that come into contact with the food or animal.

The combined use of a) monochloramine and b) at least one organic acid (and optionally at least one base or pH control agent) in aqueous solutions can also be useful in agrochemical formulations for the purpose of protecting seeds or crops against microbial spoilage.

According to the methods of the present invention, controlling or inhibiting the growth of at least one microorganism includes the reduction and/or the prevention of such growth.

It is to be further understood that by "controlling" (i.e., preventing) the growth of at least one of microorganism, the growth of the microorganism is inhibited. In other words, there is no growth or essentially no growth of the microorganism. "Controlling" the growth of at least one microorganism maintains the microorganism population at a desired level, reduces the population to a desired level (even to undetectable limits, e.g., zero population), and/or inhibits the growth of the microorganism. Thus, in the present invention, the products, material, or media susceptible to attack by the at least one microorganism can be preserved from this attack and the resulting spoilage and other detrimental effects caused by the microorganism. Further, it is also to be understood that "controlling" the growth of at least one microorganism also includes biostatically reducing and/or maintaining a low level of at least one microorganism such that the attack by the microorganism and any resulting spoilage or other detrimental effects are mitigated, i.e., the microorganism growth rate or microorganism attack rate is slowed down and/or eliminated.

When two chemical microbicides are mixed and added to the product, or added separately, three results are possible:
1) The chemicals in the product would produce an additive (neutral) effect.
2) The chemicals in the product would produce an antagonistic effect, or
3) The chemicals in the product would produce a synergistic effect.

An additive effect has no economic advantage over the individual components. The antagonistic effect would produce a negative impact. Only a synergistic effect, which is less likely than either an additive or antagonistic effect, would produce a positive effect and therefore possess economic advantages.

It is known in the microbicidal literature that there is no theoretical method to anticipate additive, antagonistic, or synergistic effects when two biocides are mixed to yield a new formulation. Nor is there a method to predict the relative proportions of the different biocides required to produce one of the three effects described above.

Thus, the combination of a) monochloramine and b) at least one organic acid (and optionally at least one base or pH control agent) in aqueous solutions preferably achieve superior, i.e. greater than additive, microbicidal activity, even at low concentrations, against a wide variety of microorganisms. Examples of these microorganisms include fungi, bacteria, algae, and mixtures thereof, such as, but not limited to, for example, *Lactobacillus, Pediococcus, Leuconostoc* and *Weissella* species, *Acetobacter* sp., *Trichoderma viride, Aspergillus niger, Pseudomonas aeruginosa, Enterobacter aerogenes, Klebsiella pneumoniae*, and *Chlorella* sp. The microorganism can be an unwanted bacterium or bacteria. The unwanted bacteria can be unwanted bacteria in ethanol fermentation, such as *Lactobacillus, Pediococcus, Leuconostoc* and *Weissella* species, *Acetobacter* sp., or others.

The combination of a) monochloramine and b) at least one organic acid of the present invention can have a low toxicity.

The monochloramine ($NH_2Cl$) (also referred to here as MCA) can be obtained or made on site. In dilute aqueous solution, chloramine is prepared by the reaction of ammonia with sodium hypochlorite:

$$NH_3 + OCl^- \rightarrow NH_2Cl + HO^-.$$

This is also the first step of the Raschig hydrazine synthesis. The reaction is carried out in a slightly alkaline medium (pH 8.5 to 11). The acting chlorinating agent in this reaction is hypochloric acid (HOCl), which has to be generated by protonation of hypochlorite, and then reacts in a nucleophilic substitution of the hydroxo against the amino group. The reaction occurs quickest at around pH 8. At higher pH values the concentration of hypochloric acid is lower, at lower pH values ammonia is protonated to form ammonium ions $NH_4^+$, which do not react further. The chloramine solution can be concentrated by vacuum distillation and by passing the vapor through potassium carbonate which absorbs the water. Chloramine can be extracted with ether. Gaseous chloramine can be obtained from the reaction of gaseous ammonia with chlorine gas (diluted with nitrogen gas):

$$2NH_3(g) + Cl_2(g) \Leftrightarrow NH_2Cl(g) + NH_4Cl(s)$$

Pure chloramine can be prepared by passing fluoroamine through calcium chloride:

$$2NH_2F + CaCl_2 \rightarrow 2NH_2Cl + CaF_2.$$

Methods for in situ chloramine generation are known which can be adapted for use in the method of the present invention. For example, rather than adding pure chloramine to the product, material, or system, sodium hypochlorite solution or chlorine can be added together with ammonia or ammonium salts to generate chloramine in situ prior to or at the time of combining with the organic acid. A single type of chloramine or combinations of different chloramines can be used.

The term "organic acid" as used herein refers to an organic compound with acidic properties. The organic acid can refer, as an option, to an acid that contains in its formula carbon, hydrogen, and oxygen, wherein carbon and oxygen form at least one carboxyl group. The organic acid can refer to compounds which can be citric acid, formic acid, acetic acid, bromoacetic acid, glycolic acid, propionic acid, glyoxylic acid, gluconic acid, lactic acid, citric acid, tartaric acid, malonic acid, maleic acid, fumaric acid, erythorbic acid, pyrrolidone carboxylic acid, sorbic acid, ascorbic acid, undecenoic acid, undecynoic acid, benzoic acid, hydroxybenzoic acid, salicylic acid, dehydracetic acid, or salts or esters thereof, or any combinations thereof. The organic acid, as preferred option, can be citric acid, or a salt or ester thereof, or any combinations thereof. Citric acid is weak organic tricarboxylic acid having the chemical formula $C_6H_8O_7$. Citric acid occurs naturally in citrus fruits, and is industrially produced. A citrate is a derivative of citric acid; that is, the salts, esters, and the polyatomic anion found in solution. As examples, salts of citric acid can be trisodium citrate, disodium hydrogen citrate, tripotassium citrate, dipotassium hydrogen citrate, monocalcium citrate, dicalcium citrate, tricalcium citrate, and an ester thereof is triethyl citrate. Acid salts of citric acid can be prepared, as an option, by adjustment of the pH before crystallizing the compound by known methods. The organic acid can be or include citric acid. Mixtures of organic acids may be used, e.g., citric acid and a different organic acid.

An organic acid can be more stable or can function better in an acidic environment, whereas MCA can function better in alkaline environment. As indicated, since some industrial processes, such as ethanol fermentation steps are usually performed under acidic pH conditions, any adjustment of aqueous solution pH to 7 or higher as part of treatment of a medium, if done as an option, preferably is performed at least in part or entirely before the fermentation step. Fermentation yeasts may not tolerate pH much below pH 3-4 or above 8-8.2 without adversely impacting the fermentation process. Ethanol fermentation processes can be treated with the aqueous solution of the present invention which combines organic acid and monochloramine with any addition of pH control agent managed to reduce or avoid adverse impacts on yeast or other components of the fermentation process.

At least one base can be present or included in the aqueous solution, as an option, to adjust, e.g., fine-tune, the pH for optimal effect or synergy between the organic acid and MCA from a biocidal efficiency standpoint, or cost perspective, or both. Any base can be used herein as a pH-adjusting adjunct for adjusting the pH (e.g., increasing pH). The base can be an alkali metal hydroxide, alkaline earth metal hydroxide, or any combination thereof. The base can be sodium hydroxide, potassium hydroxide, calcium hydroxide, barium hydroxide, magnesium hydroxide, sodium carbonate, or any combination thereof. Preferred bases for pH adjustment can include water-soluble alkalis such as sodium hydroxide, potassium hydroxide, or mixtures thereof. The base can be used as an aqueous solution. The base can be added to the aqueous solution before treatment of a product, material or medium, and/or can be added to the product, material or medium before or after treatment with the aqueous solution, or both. As indicated, the base can be used as a pH control agent. If desirable to reduce the pH, such as, e.g., to provide or maintain a pH of no greater than 12 or other pH value with a pH range of about 4 to about 12 (e.g., about 4 to 11, or 4 to 10, or 4 to 9, or 4 to 8, or 4 to 7, or 4 to 6), a pH control agent can used which is at least one acid. The at least one acid, if used, can be hydrochloric acid, sulfuric acid, or other acids, or alum, or any combination thereof.

The amount of base, if added, can be an amount which adjusts the aqueous solution to a desired pH value or range. The concentration of the base can be any commercially available concentration (e.g., 0.1 N or 0.01N, or concentrated base) and/or can be diluted to any desired or appropriate concentration. The base can be present in a concentration so that the aqueous solution has a pH of from about 4 to about 12, or from about 5 to about 12, or from about 6 to about 11, or from about 7 to about 10, or from about 7.1 to about 9.9, or from about 7.5 to about 9.5, or from about 8 to about 9, or other values.

The aqueous solution to which the at least one base can be added can be a reservoir or flowing stream of aqueous fluid which already contains monochloramine but not yet organic acid. For instance, after the at least one base is added to an aqueous fluid comprising monochloramine, the resulting base-treated aqueous fluid can be further modified by addition of the organic acid before the aqueous fluid comprising all three components is introduced into an aqueous system (or product, material, or medium) to be treated. As another option, aqueous fluid comprising the monochloramine and the least one base can be added to the aqueous system (or product, material, or medium) to be treated, and the organic acid can be separately added to the aqueous system upstream or downstream thereof. As another option, the at least one base, monochloramine, and organic acid can be separately added to an aqueous system (or product, material, or medium) to be treated, wherein the aqueous solution is essentially prepared concurrent with treatment by it. The aqueous system or medium that can be treated in any of these manners with the aqueous solution can be aqueous fluid (e.g., water alone, or water-predominant solutions, or other water-based solutions) held in a pool, vessel, or flowing aqueous fluid in a conduit or open flowing stream, or other aqueous systems. The liquid system or medium may be an animal water trough or gutter through which drinking water flows or stands. As stated, the present invention also embodies the separate addition of the monochloramine and at least one organic acid, such as citric acid, and, if used, the at least one base or pH control agent, to products, materials, or media. According to this option, the components are individually added to the products, materials, or media so that the final amount of each component present at the time of use that can preferably be that amount synergistically effective, to control the growth of at least one microorganism.

The monochloramine and at least one organic acid, and, if used, the at least one base or pH control agent, can be added separately to the product, material, or medium, or system or environment that contains the product, material or medium. When adding separately, each of the monochloramine and organic acid, and, if used, the at least one base or pH control agent, can be added simultaneously, almost simultaneously (within 0.1 sec to 5 minutes of each other, for instance within 5 seconds, within 10 seconds, within 30 seconds, within 1 minute, within 2 minutes, within 5 minutes, or within 10 minutes of each other), or in sequence and in any order (e.g., organic acid first or monochloramine first). Further, in this option or in any embodiment of the present invention, the monochloramine can be formed in-situ in the presence of (or just before the MCA contacts) the product, material, or medium being treated or protected. The in-situ formation of the monochloramine can be done before or after organic acid is present. After adding (or forming) each of the monochloramine and organic acid, and, if used, the at least one base or pH control agent, in a liquid solution, medium or environment, mixture or agitation can be optionally used to mix the two (or three) components together for any amount of time (e.g., 1 second to 10 minutes or more). Each component can be applied by spraying, misting, coating, dipping, or any other technique/application that permits the contacting of the product, material, medium or system with each of a) monochloramine and b) at least one organic acid.

The microbicides in the aqueous solution of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. The solvent can be selected from water, glycols, glycol ethers, esters and mixtures thereof. Citric acid can be used in commercially available or synthesized forms in aqueous concentrates or dilute aqueous solutions, such as in concentrations of from about 3 wt. % to about 98 wt. %, or from about 10 wt. % to about 85 wt. %, or from about 15 wt. % to about 70 wt. %, or from about 20 wt. % to about 60 wt. %, or about 25 wt. % to about 50 wt. %, or other concentrations. Powdered salts of citric acid can be dissolved in water or an aqueous medium. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

The components (a) monochloramine (MCA) and (b) at least one organic acid (and optionally the at least one base or pH control agent) also can be formulated in the form of a dispersion. The solvent component of the dispersion can be an organic solvent or water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and/or anti-corrosion additives.

When components (a) monochloramine (MCA) and (b) at least one organic acid (and optionally the at least one base or pH control agent) are formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

For purposes of the present invention, the formulation of the present invention can be in the absence of other microbicides, and/or in the absence of metal containing compounds, and/or in the absence of peroxides, and/or in the absence of antibiotics, and/or in the absence of surfactants, and/or in the absence of any actives other than monochloramine and organic acid.

As described above, components (a) monochloramine (MCA) and (b) at least one organic acid (and optionally the at least one base or pH control agent) are preferably used in aqueous solution in synergistically effective amounts. The weight ratios of (a) to (b) vary depending on the type of microorganisms and product, material, or media to which the aqueous solution is applied. In view of the present invention, one skilled in the art can readily determine, without undue experimentation, the appropriate weight ratios for a specific application. The weight ratio (wt:wt basis) of component (a) to component (b) used in aqueous solution or formulation ranges from 1:1 to 1:2500, or 1:5 to 1:2500, or from 1:5 to 1:2250, or from 1:5 to 1:2000, or from 1:5 to 1:1500, or from 1:5 to 1:1000, or from 1:5 to 1:750, or from 1:5 to 1:500, or from 1:5 to 1:250, or from 1:5 to 1:100, or from 1:5 to 1:90, or from 1:5 to 1:80, or from 1:5 to 1:75, or from 1:5 to 1:70, or from 1:5 to 1:60, or from 1:5 to 1:50, or from 1:5 to 1:40, or from 1:5 to 1:30, or from 1:5 to 1:25, or from 1:5 to 1:15, or from 1:5 to 1:10. These weight ratios can be for the aqueous solution to be treated and/or can be the weight ratios of the aqueous solution prepared and used to treat an aqueous solution. These dosages and others described herein can be calculated or measured values or can be considered residual concentrations in the aqueous solution.

For instance, in an aqueous solution or formulation, the MCA can be present at a concentration of from 0.1 ppm to 50,000 ppm, or from 0.1 ppm to 10,000 ppm, or from 0.1 ppm to 5,000 ppm, or from 0.1 ppm to 1,000 ppm, or from 0.1 ppm to 750 ppm, or from 0.1 ppm to 500 ppm, or from 0.1 ppm to 250 ppm, or from 0.1 ppm to 100 ppm, or from 0.1 ppm to 75 ppm, or from 0.1 ppm to 50 ppm, or from 1 ppm to 5,000 ppm, or from 1 ppm to 1,000 ppm, or from 1 ppm to 750 ppm, or from 1 ppm to 450 ppm, or from 1 ppm to 250 ppm, or from 5 ppm to 250 ppm, or from 10 ppm to 250 ppm, or from 15 ppm to 250 ppm, or from 20 ppm to 250 ppm, or from 25 ppm to 250 ppm, or from 1 ppm to 225 ppm, or from 1 ppm to 200 ppm, or from 1 ppm to 175 ppm, or from 1 ppm to 150 ppm, or from 1 ppm to 100 ppm, or from 1 ppm to 75 ppm, or from 1 ppm to 50 ppm, or from 5 ppm to 150 ppm, or from 10 ppm to 150 ppm, or from 15 ppm to 150 ppm, or from 20 ppm to 150 ppm, or from 25 ppm to 150 ppm, or from 50 ppm to 150 ppm, or from 5 ppm to 125 ppm, or from 5 ppm to 100 ppm, or from 5 ppm to 75 ppm, or from 5 ppm to 50 ppm, or from 10 ppm to 100 ppm, or from 15 ppm to 100 ppm, or from 20 ppm to 100 ppm, or from 25 ppm to 100 ppm, or from 50 ppm to 100 ppm, or from 10 ppm to 90 ppm, or from 10 ppm to 75 ppm, or from 10 ppm to 50 ppm, or from 10 ppm to 25 ppm, or from 15 ppm to 80 ppm, or from 25 ppm to 80 ppm, or from 15 ppm to 75 ppm, or from 15 ppm to 60 ppm, or from 15 ppm to 50 ppm, or from 20 ppm to 60 ppm, or from 25 ppm to 50 ppm, and the organic acid can be present at a concentration of 0.1 ppm to 50,000 ppm, or from 0.1 ppm to 25,000 ppm, or from 0.1 ppm to 20,000 ppm, or from 0.1 ppm to 15,000 ppm, or from 0.1 ppm to 10,000 ppm, or from 0.1 ppm to 5,000 ppm, or from 0.1 ppm to 3,000 ppm, or from 0.1 ppm to 1,000 ppm, or from 0.1 ppm to 750 ppm, or from 0.1 ppm to 500 ppm, or from 0.1 ppm to 250 ppm, or from 0.1 ppm to 100 ppm, or from 0.1 ppm to 75 ppm, or from 0.1 ppm to 50 ppm, or from 1 ppm to 45,000 ppm, or from 5 ppm to 40,000 ppm, or from 10 ppm to 35,000 ppm, or from 50 ppm to 30,000 ppm, or from 100 ppm to 25,000 ppm, or from 250 ppm to 20,000 ppm, or from 300 ppm to 10,000 ppm, or from 400 ppm to 5,000 ppm, or from 500 ppm to 3,000 ppm, or from 750 ppm to 2,500 ppm. These ppm concentrations can be for an aqueous solution to be treated and/or can be the ppm concentrations of the aqueous solution prepared and used to treat an aqueous solution.

In general, for the aqueous solution having a pH of from about 4 to about 12 and, if used, base or pH control agent, a synergistically microbicidally effective response (e.g., fungicidal, bactericidal, or algicidal response) can be obtained when the combination of component (a) and component (b) is employed in concentrations ranging about 0.1 ppm to 5% (i.e., 50,000 ppm) of the MCA, preferably from 0.1 ppm to 750 ppm, more preferably from 1 ppm to 450 ppm, even more preferably from 1 ppm to 250 ppm, and most preferably from 1 ppm to 100 ppm; and from 0.1 ppm to 50,000 ppm of the organic acid (e.g., citric acid), preferably from 0.1 ppm to 25,000 ppm, more preferably 100 ppm to 25,000 ppm, even more preferably 250 ppm to 10,000 ppm, and most preferably 500 ppm to 5,000 ppm. In general, an effective fungicidal, bactericidal, or algicidal response can be obtained when the synergistic combination is employed in concentrations ranging about 0.1 ppm to 1% (i.e., 10,000 ppm) of the MCA, preferably 0.1 ppm to 750 ppm, more preferably 1 ppm to 450 ppm, and most preferably from 1 ppm to 100 ppm; and from about 0.1 ppm to 25,000 ppm of the organic acid (e.g., citric acid), preferably 100 ppm to 25,000 ppm, more preferably 250 ppm to 10,000 ppm, and most preferably, 500 ppm to 5,000 ppm. These ppm concentrations can be for the aqueous solution to be treated and/or can be the ppm concentrations of the aqueous solution prepared and used to treat an aqueous solution.

Depending upon the specific application, the aqueous solution can be prepared in liquid form by dissolving, dispersing, or in-situ forming the monochloramine and at least one organic acid, and, if used, at least one base or pH control agent, in water or other aqueous fluid. The preservative containing the aqueous solution of the present invention may be prepared in an emulsion form by emulsifying it in water, or if necessary, by adding a surfactant. Additional chemicals, such as insecticides, may be added to the foregoing preparations and aqueous solutions depending upon the intended use of the preparation.

The mode as well as the rates of application of the aqueous solution of this invention could vary depending upon the intended use. The aqueous solution could be applied by spraying or brushing onto the material or product. The material or product in question could also be treated by dipping in a suitable formulation of the aqueous solution. In a liquid or liquid-like medium, the aqueous solution could be added into the medium by pouring, or by metering with a suitable device so that a solution or a dispersion of the aqueous solution can be produced.

Fermentation systems which can be can be treated with the synergistic microbicidal combination of the present invention include systems for production of ethanol fermentation systems and pharmaceutical fermentations systems, or other fermentation systems. The fermentable carbohydrate-containing feedstock that can be treated in these fermentations systems can comprise fermentable carbohydrate derived from cereal grain, cellulose, fruit, or non-cereal grain vegetable, or any combinations thereof. The ethanol fermentations systems can include those for corn ethanol, cane-to-ethanol, dry grind ethanol, wet grain ethanol, wheat-to-ethanol, barley-to-ethanol, oats-to-ethanol, rye-to-ethanol, sorghum-to-ethanol, cellulosic-to-ethanol, sugar beet-to-ethanol, rice-to-ethanol, or other ethanol fermentation systems.

A method according to the present invention can be practiced in conventional ethanol production plants with modifications that can be easily made in view of the present invention. Referring to FIG. 1, a process for treating an ethanol fermentation system with the synergistic microbicidal combination of the present invention is generally shown as directed to introducing combinations of citric acid or other organic acid and monochloramine (MCA) in combinations or to provide combinations thereof in the system via one or more of introduction locations (42), (43), (44), (46), (47), (49), wherein other exemplary features of the system, as an option, include (1) coarse milling (10) to generate milled corn (15), and the milled corn (15) can be combined with α-amylase or other liquefaction enzyme and water (21) in a mix tank (20) in a pre-liquefaction step to form pre-liquified corn mash (25). The pre-liquified corn (25) can be fed to a jet heater (30) for heat liquefaction to generate heat-liquified corn mash (35), and the heat-liquified corn mash (35) can be combined with α-amylase (and/or other liquefying enzyme) and water (41) in a holding vessel (40) in a digest step to generate liquified corn mash (45). A portion of the liquified corn mash (45) can be combined with glucoamylase and/or other saccharifaction enzyme, a nutrient source, yeast, and water (51) in a propagation tank (50) to generate pitching yeast (55), which can be fed to fermenter vessel (60). The rest of the liquefied corn mash (45) can be fed through piping (48) to fermenter vessel (60). This portion of the liquified corn (45) fed through piping (48), with the pitching yeast (55) and glucoamylase, a nitrogen-containing nutrient source and water (61) can be combined in the fermenter vessel (60) to generate a fermentation composition (65). The fermentation composition can be sent to a beer well (70), then to a reboiler (80) for recovery of crude ethanol (95) from the overhead stream (85) in a condenser (90). The crude ethanol (95) can be sent to a molecular sieve unit (100) for separation of ethanol (105) from byproducts (106). The stillage or reboiler bottoms (87) can be sent to a centrifuge (110) where wet distiller grain solids ("DGS") (115) and centrifugate (117) (liquid-containing fraction) are separated. All or a portion of the centrifugate (117) can optionally be recycled to the mix tank (20), propagation tank (50) and/or fermenter (60) as backset. The centrifugate (117) that is not recycled can be fed to an evaporator (130) where it can be concentrated to produce syrup (135), and the syrup (135) can be combined with the wet DGS (115) and the combination is sent to a dryer (120) in which DDGS (125) can be prepared. In an alternative, wet DGS (115) can be dried in the absence of syrup (135) to generate dried distillers grain ("DDG") (not shown). To simplify the illustration in FIG. 1, additional pumps, heat exchangers, and other conventional equipment that can be used in the process are not shown.

As shown in FIG. 1, as an option, the organic acid and monochloramine can be added in synergistically effective combined amounts at one or more locations (44), (42), (43), (47) before the fermentation vessel (60), (46) in the fermentation vessel (60), at one or more locations (49) after the fermentation vessel (60), or any combinations thereof. As a preferred option, the organic acid and monochloramine are added in a synergistically effective combined amount at least at one or more locations before the fermentation vessel (60) (e.g., at least at one or more of locations (44), (42), (43), (47)). The treatment can be performed, with or without pH adjustment, on the fermentable carbohydrate-containing feedstock before introduction to fermentation vessel (60) in holding vessel (40), piping (48), propagator (50) (not shown) or other process units/equipment (e.g., pumps), or in any combinations of these options. The organic acid and monochloramine can be added from the same aqueous solution into holding vessel (40), piping (48) (e.g., using 42 and alternate line shown in dashes for 43), or into the backset line (47), or any combinations of these or other process equipment located in advance of the fermentation vessel (60). The organic acid and monochloramine can be added separately to the fermentable carbohydrate-containing feedstock in holding vessel (40), or separately into piping (48) as shown by (42) and (43) in FIG. 1, or separately into the backset line (47), or any combinations of these or other process equipment located in advance of the fermentation vessel (60). The organic acid and monochloramine can be added from the same aqueous solution or separately (44) into holding vessel (40), and then additional monochloramine (43) can be added in piping (48) to the mash discharged from holding vessel (40). Mixing of separately introduced organic acid and monochloramine in the feedstock or other process fluid upstream of the fermentation vessel can be provided with turbulence present in process units by agitators therein, or by pumps, or in-line static mixers in piping, or by introducing the organic acid and monochloramine ahead of a bend or bends in the piping that encourage turbulence in the fluids passing through the piping, or other equipment arrangements or combinations of these. The combined organic acid and monochloramine may survive about 5 to about 10 minutes, or other periods of time, in the treated process system in the presence of an organic load (e.g., fermentable carbohydrate-containing feedstock). By adding the organic acid and monochloramine components to process fluid at a location or locations sufficiently near the fermentation vessel, from a temporal standpoint, before introduction into the fermentation vessel, control of lactic acid, acetic acid or both in the fermentation vessel during fermentation may be provided even if the organic acid and monochloramine are not added directly into the fermentation vessel (which is another option of the present invention). The organic acid and monochloramine can be introduced into the fermentation vessel (60) as indicated by (46) from a single aqueous solution or separately. The organic acid and monochloramine can be introduced into the fermented composition (65) after discharge from the fermentation vessel (60) as indicated by (49) (e.g., at a beer well as shown or other post-fermentation process unit/equipment or piping) from a single aqueous solution or separately.

Other aspects, equipment and details of the ethanol fermentation chemistry, process and system can be based on those used in ethanol production plants, such as those described in U.S. Pat. No. 8,951,960 and U.S. Patent Application Publication No. 2017/0107543, which are incorporated herein in their entireties by reference.

The microbicidal and synergistic activity of the combinations described above has been confirmed using standard laboratory techniques as illustrated below. The following examples are intended to illustrate, not limit, the present invention.

EXAMPLE 1

Laboratory experiments were performed to study the microbicidal efficacy of a combination of monochloramine with citric acid. In this study, monochloramine ("oxamine" or MCA) and citric acid were evaluated for synergism effect against *Pseudomonas* bacterial cells.

*Pseudomonas* bacterial cells were grown in nutrient broth media. The nutrient broth media comprised corn mash (35 wt %) and water. Appropriate amount of culture cells, monochloramine and/or citric acid were transferred into 24-well plate and incubated at 37° C. The 24-well plate layout held samples which contained monochloramine added in concentrations (ppm) of 0.00, 12.50, 50.00 and 100.00 in different rows of well samples, and citric acid added in concentrations (ppm) of 0, 500, 3,000, 7,000, and 10,000 ppm, in different columns of well samples, in a checkerboard pattern, such as shown in Tables 1 and 2. Bacterial growth was monitored for each sample at 12 hours and 14 hours. Measurement was qualitative based upon measurement in a plate reader. A UV-VIS spectrophotometer was used at measurement wavelength 600 nm.

TABLE 1

| Bacterial growth at 12 hr. | | | | | | |
|---|---|---|---|---|---|---|
| Oxamine | Citric acid (CA), ppm | | | | | |
| (MCA), ppm | 0 | 500 | 1000 | 3000 | 7000 | 10000 |
| 0 | +++ | +++ | +++ | +++ | +++ | +++ |
| 12.5 | +++ | +++ | +++ | +++ | +++ | +++ |
| 50 | +++ | --- | +++ | --- | +++ | --- |
| 100 | --- | --- | --- | --- | --- | --- |

Symbol Key:
--- No further growth observed.
+++ Growth observed.

TABLE 2

| | Bacterial growth at 14 hr. | | | | | |
|---|---|---|---|---|---|---|
| Oxamine | Citric acid (CA), ppm | | | | | |
| (MCA), ppm | 0 | 500 | 1000 | 3000 | 7000 | 10000 |
| 0 | +++ | +++ | +++ | +++ | +++ | +++ |
| 12.5 | +++ | +++ | +++ | +++ | +++ | +++ |
| 50 | +++ | --- | +++ | +++ | +++ | --- |
| 100 | --- | --- | --- | --- | --- | --- |

Symbol key:
Same as table 1.

The results of the study showed that 10,000 ppm citric acid and 50 ppm monochloramine, when added individually, are not inhibitory to bacterial growth but when used in combination bacterial growth is stopped. Similar observations were made for 500 ppm and 3000 ppm citric with 50 ppm monochloramine. For this study, the data shows that 10,000 ppm citric acid is not capable of limiting growth in the absence of MCA. Conversely, 100 ppm of MCA is sufficient to control. In the case of the 50 ppm MCA treatment, there are wells co-treated at 500 ppm and 10000 ppm that show control. In the case where control is achieved in co-treated wells, the single treatments were insufficient, and this is an indication of synergistic effect.

EXAMPLE 2

Monochloramine and citric acid, and combinations of them, were evaluated for synergistic effect against *Pseudomonas* bacterial cells in a laboratory experiment.

In this study, *Pseudomonas* bacterial cells were grown in nutrient broth media. The nutrient broth media comprised corn mash (35 wt %) and water. Appropriate amount of culture cells, monochloramine and/or citric acid were transferred into 24-well plate and incubated at 37° C. for 48 hrs. in a plate reader. The 24-well plate layout held samples which contained monochloramine added in concentrations (ppm) of 0, 12.5, 50 and 100 ppm in different rows of well samples, and citric acid added in concentrations (ppm) of 0, 500, 3,000, 7,000, 10,000, and 20,000 in different columns of well samples, in a checkerboard pattern. Bacterial growth was monitored for each sample using a UV-VIS spectrophotometer to measure optical density (OD) (at measurement wavelength 600 nm) for the samples for 48 hours. The growth curves from the data are plotted in FIGS. 2-5.

Figure 2:
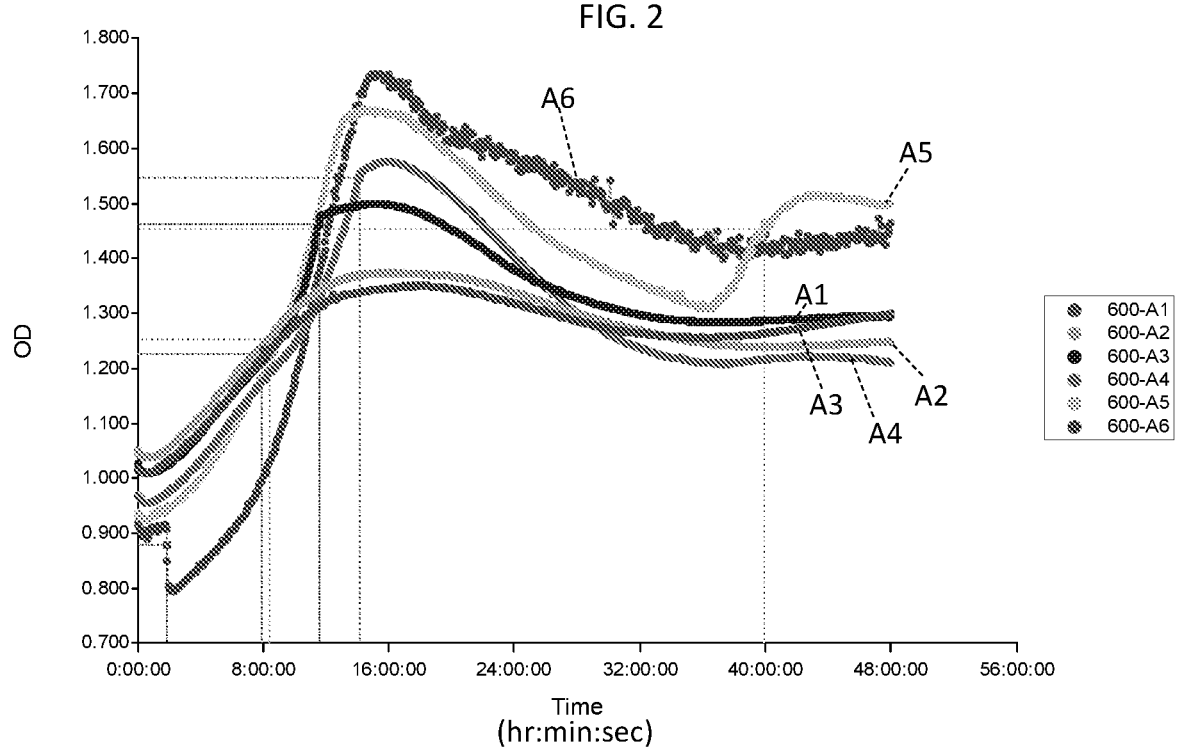
FIG. 2 is a graph plotting bacterial growth, as determined from optical density (OD, at 600 nm) measurements, with respect to time (hours:minutes:seconds) in nutrient broth media treated with citric acid alone (no monochloramine added) at different concentrations as comparison examples, and for a control sample with no treatment.

For the data set collected and plotted in FIG. 2, the bacterial growth was measured for the following samples, which were treated with citric acid (CA) alone (no monochloramine (MCA) added) at different concentrations as comparison examples, and for a control sample with no treatment: A1—no treatment; A2—0 ppm MCA/500 ppm CA; A3—0 ppm MCA/3000 ppm CA; A4—0 ppm MCA/7000 ppm CA; A5—0 ppm MCA/10,000 ppm CA; A6—0 ppm MCA/20,000 ppm CA.

Figure 3:
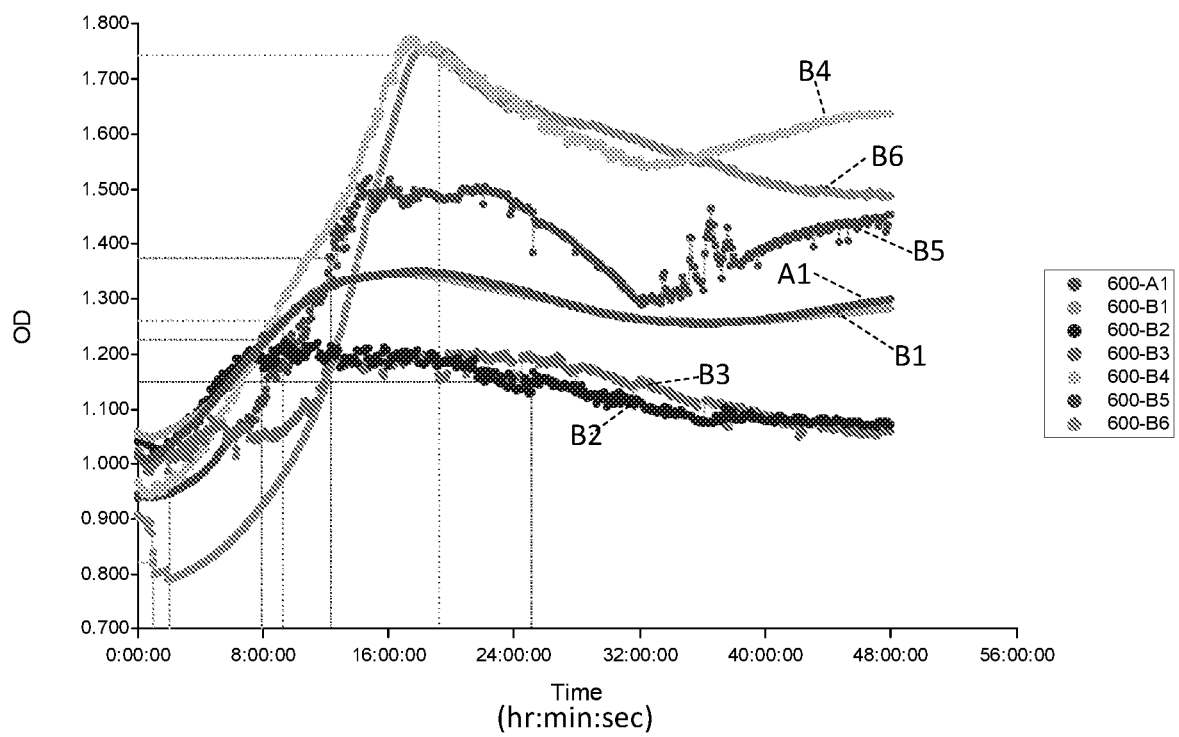
FIG. 3 is a graph plotting bacterial growth, as determined from optical density (OD, at 600 nm) measurements, with respect to time (hours:minutes:seconds) in nutrient broth media treated with 12.5 ppm monochloramine ("oxamine") and citric acid at different concentrations according to embodiments of the present invention, and for a control sample with no treatment.

For the data set collected and plotted in FIG. 3, the bacterial growth was measured for the following samples, which were treated with 12.5 ppm monochloramine (MCA) and citric acid (CA) at different concentrations, and for a control sample with no treatment: A1—no treatment; B1—12.5 ppm MCA only; B2—12.5 ppm MCA/500 ppm CA; B3—12.5 ppm MCA/3000 ppm CA; B4—12.5 ppm MCA/7000 ppm CA; B5—12.5 ppm MCA/10,000 ppm CA; B6—12.5 ppm MCA/20,000 ppm CA.

Figure 4:
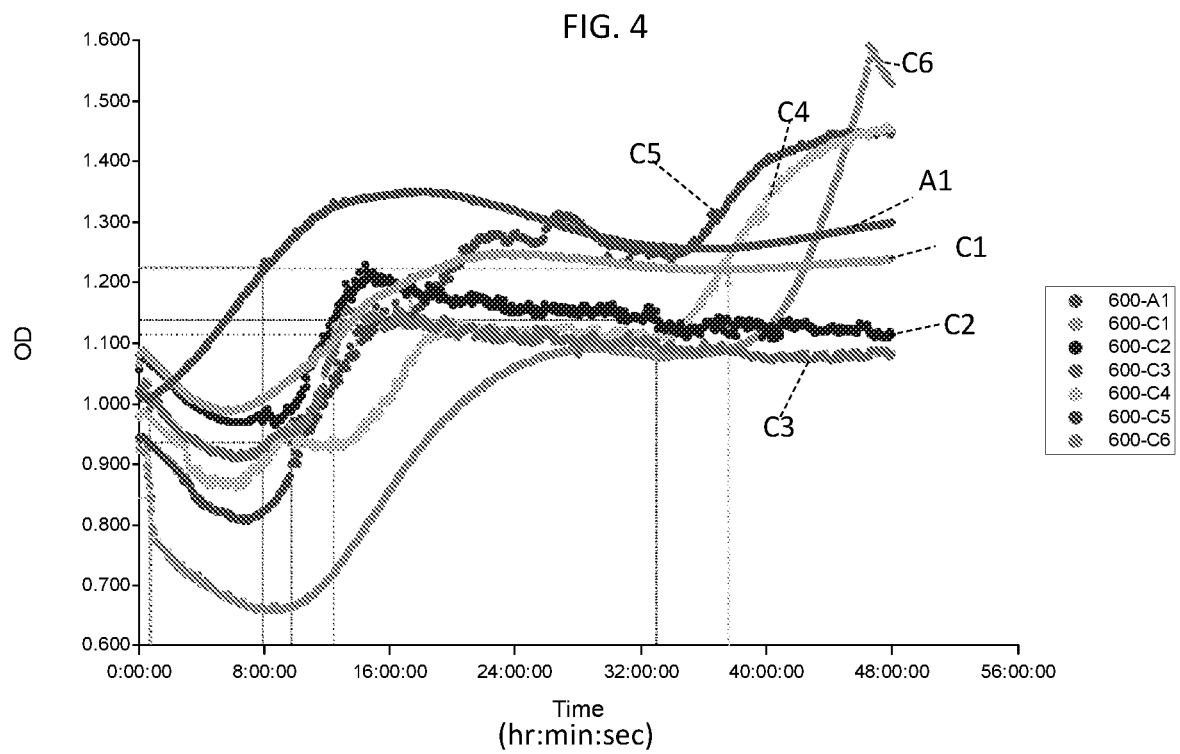
FIG. 4 is a graph plotting bacterial growth, as determined from optical density (OD, at 600 nm) measurements, with respect to time (hours:minutes:seconds) in nutrient broth media treated with 50 ppm monochloramine ("oxamine") and citric acid at different concentrations according to embodiments of the present invention, and for a control sample with no treatment.

For the data set collected and plotted in FIG. 4, the bacterial growth was measured for the following samples, which were treated with 50 ppm monochloramine (MCA) and citric acid (CA) at different concentrations, and for a control sample with no treatment: A1—no treatment; C1—50 ppm MCA only; C2—50 ppm MCA/500 ppm CA; C3—50 ppm MCA/3000 ppm CA; C4—50 ppm MCA/7000 ppm CA; C5—50 ppm MCA/10,000 ppm CA; C6—50 ppm MCA/20,000 ppm CA.

Figure 5:
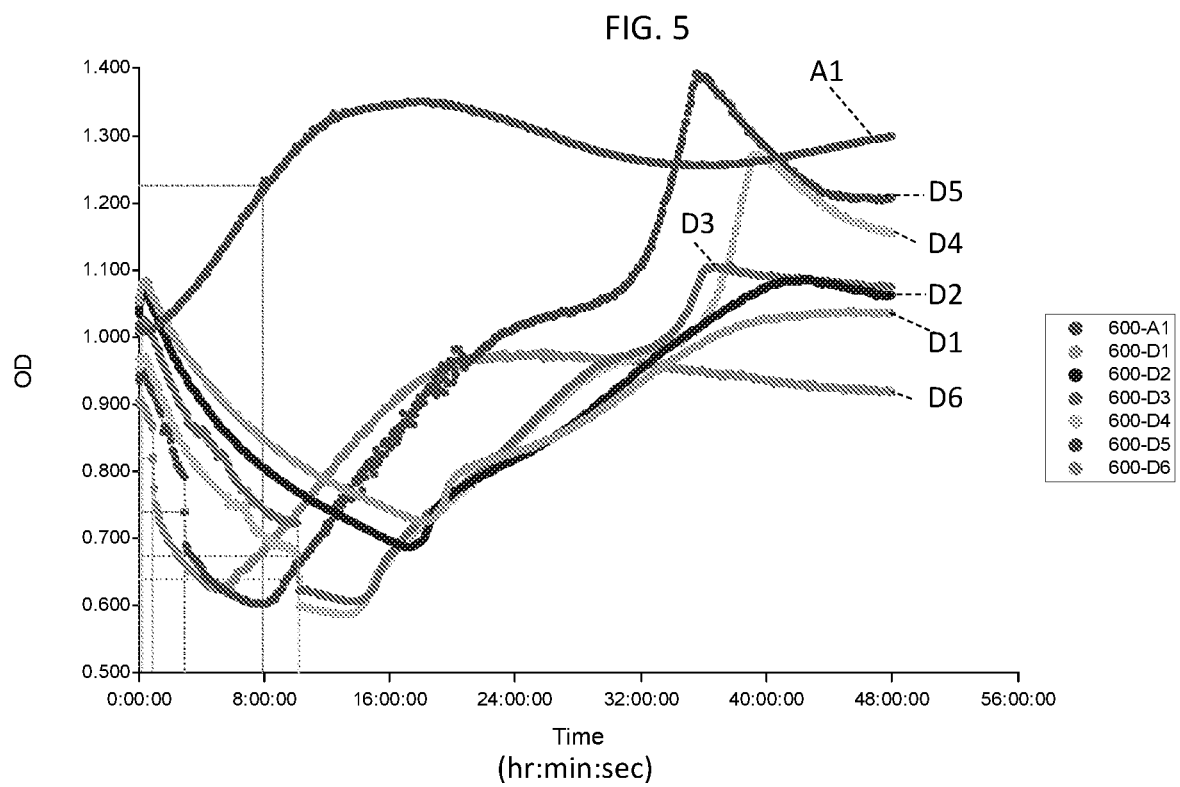
FIG. 5 is a graph plotting bacterial growth, as determined from optical density (OD, at 600 nm) measurements, with respect to time (hours:minutes:seconds) in nutrient broth media treated with 100 ppm monochloramine ("oxamine") and citric acid at different concentrations according to embodiments of the present invention, and for a control sample with no treatment.

For the data set collected and plotted in FIG. 5, the bacterial growth was measured for the following samples, which were treated with 100 ppm monochloramine (MCA) and citric acid (CA) at different concentrations, and for a control sample with no treatment: A1—no treatment; D1—100 ppm MCA only; D2—100 ppm MCA/500 ppm CA; D3—100 ppm MCA/3000 ppm CA; D4—100 ppm MCA/7000 ppm CA; D5—100 ppm MCA/10,000 ppm CA; D6—100 ppm MCA/20,000 ppm CA.

The results in FIG. 2 show that not all of the evaluated citric acid concentrations controlled bacteria growth when used alone. The results in FIG. 3 show that monochloramine at 12.5 ppm showed no control of bacteria growth when used alone or in combination with different citric acid concentrations. The results in FIG. 4 show that for 50 ppm monochloramine treatments, the cells growth was delayed but when combined with different levels of citric acid there was significant synergistic inhibition of bacteria growth. The results in FIG. 5 show that monochloramine at 100 ppm dosage levels showed total inhibition of bacteria growth with and without citric acid. Monochloramine and citric acid showed synergistic effect against the growth of *Pseudomonas* bacteria cells. Monochloramine is an oxidizing chemistry based product that gets greatly broken down in reductive environment. However, the results of this study show that combining monochloramine with citric acid can synergistically increase its efficacy against bacteria growth and contamination.

The present invention includes the following aspects/embodiments/features in any order and/or in any combination:

1. A method of controlling the growth of at least one microorganism in or on a product, material, or medium susceptible to attack by a microorganism, the method comprising treating the product, material or medium with aqueous solution comprising (a) monochloramine and (b) at least one organic acid, wherein components (a) and (b) are present in a synergistically microbicidally effective combined amount to control the growth of at least one microorganism.

2. The method of any preceding or following embodiment/feature/aspect, wherein the material or medium is fermentable mash or solution, wood pulp or paper, wood chips, lumber, paints, leathers, adhesives, coatings, animal hides, tanning liquor, paper mill liquor, fiberglass, dairy processing, poultry processing, meat packing facilities, meat processing, metalworking fluids, petrochemicals, pharmaceutical formulations, cooling water, recreational water, dyes, clays, mineral slurries, cationic surfactants, formulations with cationic surfactants, influent water, waste water, pasteurizers, retort cookers, cosmetic formulations, toiletry formulations, textiles, geological, drilling lubricants, or agrochemical compositions for crop or seed protection.

3. The method of any preceding or following embodiment/feature/aspect, wherein the microorganism is bacteria, fungi, algae or combinations thereof.

4. The method of any preceding or following embodiment/feature/aspect, wherein the material or medium is in the form of a solid, a dispersion, an emulsion, a mash, a slurry, or a solution.

5. The method of any preceding or following embodiment/feature/aspect, wherein the organic acid is citric acid, or a salt or ester thereof, or any combinations thereof.

6. A method to control growth of at least one contaminant microorganism in a fermentable carbohydrate-containing feedstock comprising contacting the fermentable carbohydrate-containing feedstock with (a) monochloramine and (b) at least one organic acid, wherein components (a) and (b) are present in a synergistically microbicidally effective combined amount to control the growth of at least one contaminant microorganism in the fermentable carbohydrate-containing feedstock.

7. The method of any preceding or following embodiment/feature/aspect, wherein the monochloramine is present in the fermentable carbohydrate-containing feedstock at a concentration of 0.1 ppm to 750 ppm, and the at least one organic acid is present in the fermentable carbohydrate-containing feedstock at a concentration of 0.1 ppm to 25,000 ppm.

8. The method of any preceding or following embodiment/feature/aspect, wherein the monochloramine is present in the fermentable carbohydrate-containing feedstock at a concentration of 1 ppm to 450 ppm, and the at least one organic acid is present in the fermentable carbohydrate-containing feedstock at a concentration of 100 ppm to 25,000 ppm.

9. The method of any preceding or following embodiment/feature/aspect, wherein the monochloramine and the at least one organic acid are added to the fermentable carbohydrate-containing feedstock in a ratio of 1:5 to 1:2500.

10. The method of any preceding or following embodiment/feature/aspect, wherein the organic acid is citric acid, formic acid, acetic acid, bromoacetic acid, glycolic acid, propionic acid, glyoxylic acid, gluconic acid, lactic acid, citric acid, tartaric acid, malonic acid, maleic acid, fumaric acid, erythorbic acid, pyrrolidone carboxylic acid, sorbic acid, ascorbic acid, undecenoic acid, undecynoic acid, benzoic acid, hydroxybenzoic acid, salicylic acid, dehydracetic acid, or salts or esters thereof, or any combinations thereof.

11. The method of any preceding or following embodiment/feature/aspect, wherein the organic acid is citric acid, or a salt or ester thereof, or any combinations thereof.

12. The method of any preceding or following embodiment/feature/aspect, wherein the microorganism is a bacterium.

13. The method of any preceding or following embodiment/feature/aspect, wherein the fermentable carbohydrate-containing feedstock comprises fermentable carbohydrate derived from cereal grain, cellulose, fruit, non-cereal grain vegetable, or any combinations thereof.

14. A method for producing ethanol by fermentation with controlled growth of contaminant microorganisms comprising:
a) adding (a) monochloramine and (b) at least one organic acid to fermentable carbohydrate-containing feedstock to provide treated feedstock, wherein components (a) and (b) are present in a synergistically microbicidally effective combined amount to control the growth of at least one contaminant microorganism in the treated feedstock;
b) fermenting the treated feedstock in the presence of yeast in a vessel to produce fermented mash comprising ethanol and a solids content; and
c) distilling the fermented mash to separate at least a portion of the ethanol from stillage comprising said solids content.

15. The method of any preceding or following embodiment/feature/aspect, wherein the monochloramine and the at least one organic acid are added to the fermentable carbohydrate-containing feedstock before, after, or both before and after the feedstock is introduced into the fermenter vessel and present with the yeast.

16. The method of any preceding or following embodiment/feature/aspect, wherein the monochloramine and the at least one organic acid are added to the fermentable carbohydrate-containing feedstock before the feedstock is introduced into the fermenter vessel and present with the yeast.

17. The method of any preceding or following embodiment/feature/aspect, wherein at least a portion of the at least one organic acid is added to the fermentable carbohydrate-containing feedstock before adding the monochloramine to the fermentable carbohydrate-containing feedstock.

18. The method of any preceding or following embodiment/feature/aspect, further comprising providing a holding vessel upstream of the fermenter vessel where the fermentable carbohydrate-containing feedstock is temporarily held before conducted through piping to the fermenter vessel, wherein the monochloramine and the at least one organic acid is added to the fermentable carbohydrate-containing feedstock in both the holding vessel and in the piping before introduced into the fermenter vessel.

19. The method of any preceding or following embodiment/feature/aspect, wherein the adding of the (a) monochloramine and the (b) at least one organic acid to the fermentable carbohydrate-containing feedstock is provided without reducing yeast population of yeast present in the vessel used for the fermenting.

20. The method of any preceding or following embodiment/feature/aspect, wherein the adding of the (a) monochloramine and the (b) at least one organic acid to the fermentable carbohydrate-containing feedstock reduces total lactic acid and acetic acid produced in the fermenting compared to fermenting in the absence of adding compounds (a) and (b) to the fermentable carbohydrate-containing feedstock.

21. The method of any preceding or following embodiment/feature/aspect, wherein the fermenting is performed in the absence of added antibiotic.

22. The method of any preceding or following embodiment/feature/aspect, wherein the fermentable carbohydrate-containing feedstock comprises flowable carbohydrate-containing feedstock derived from corn in an aqueous medium.

23. The method of any preceding or following embodiment/feature/aspect, wherein the microorganism is a bacterium.

24. The method of any preceding or following embodiment/feature/aspect, wherein the monochloramine is added to the fermentable carbohydrate-containing feedstock at a concentration of 0.1 ppm to 750 ppm, and the at least one organic acid is added to the fermentable carbohydrate-containing feedstock at a concentration of 0.1 ppm to 25,000 ppm.

25. The method of any preceding or following embodiment/feature/aspect, wherein the monochloramine is present in the fermentable carbohydrate-containing feedstock at a concentration of 15 ppm to 150 ppm, and the at least one organic acid is present in the fermentable carbohydrate-containing feedstock at a concentration of 100 ppm to 25,000 ppm.

26. The method of any preceding or following embodiment/feature/aspect, wherein the monochloramine and the at least one organic acid are added to the fermentable carbohydrate-containing feedstock in a weight ratio of 1:5 to 1:2500.

27. The method of any preceding or following embodiment/feature/aspect, wherein the organic acid is citric acid, formic acid, acetic acid, bromoacetic acid, glycolic acid, propionic acid, glyoxylic acid, gluconic acid, lactic acid, citric acid, tartaric acid, malonic acid, maleic acid, fumaric acid, erythorbic acid, pyrrolidone carboxylic acid, sorbic acid, ascorbic acid, undecenoic acid, undecynoic acid, benzoic acid, hydroxybenzoic acid, salicylic acid, dehydracetic acid, or salts or esters thereof, or any combinations thereof.

28. The method of any preceding or following embodiment/feature/aspect, wherein the organic acid is citric acid, or a salt or ester thereof, or any combinations thereof.

29. The method of any preceding or following embodiment/feature/aspect, wherein the pH of the fermentable carbohydrate-containing feedstock is from about 4 to about 7.

30. The method of any preceding or following embodiment/feature/aspect, further comprising the steps of:
    d) separating the stillage into a liquids-containing fraction and a solids-containing fraction;
    e) optionally recycling at least portion of the liquids-containing fraction of d) into the fermenter vessel;
    f) recovering the solids-containing fraction of d) with drying of at least a portion of the solids-containing fraction to produce evaporated vapors and distillers dried grains product free of antibiotics.

31. An aqueous solution comprising (a) monochloramine and (b) at least one organic acid, wherein components (a) and (b) are present in a synergistically microbicidally effective combined amount to control the growth of at least one microorganism.

32. The aqueous solution of any preceding or following embodiment/feature/aspect, wherein the monochloramine is present in the aqueous solution at a concentration of 0.1 ppm to 750 ppm, and the at least one organic acid is present in the aqueous solution at a concentration of 0.1 ppm to 25,000 ppm.

33. The aqueous solution of any preceding or following embodiment/feature/aspect, wherein the monochloramine is present in the aqueous solution at a concentration of 1 ppm to 750 ppm, and the at least one organic acid is present in the aqueous solution at a concentration of 100 ppm to 25,000 ppm.

34. The aqueous solution of any preceding or following embodiment/feature/aspect, claim 31, wherein the monochloramine and the at least one organic acid are added to the aqueous solution in a weight ratio of 1:5 to 1:2500.

35. The aqueous solution any preceding or following embodiment/feature/aspect, wherein the organic acid is citric acid, formic acid, acetic acid, bromoacetic acid, glycolic acid, propionic acid, glyoxylic acid, gluconic acid, lactic acid, citric acid, tartaric acid, malonic acid, maleic acid, fumaric acid, erythorbic acid, pyrrolidone carboxylic acid, sorbic acid, ascorbic acid, undecenoic acid, undecynoic acid, benzoic acid, hydroxybenzoic acid, salicylic acid, dehydracetic acid, or salts or esters thereof, or any combinations thereof.

36. The aqueous solution of any preceding or following embodiment/feature/aspect, wherein the organic acid is citric acid, or a salt or ester thereof, or any combinations thereof.

37. The method or aqueous solution or formulation for any preceding or following embodiment/feature/aspect wherein said monochloramine and said at least one organic acid are present in a synergistically microbicidally effective combined amount to control the growth of at least one microorganism, wherein said synergistically microbicidally effective combined amount is demonstrated by a formula of $Q_A/Q_a + Q_B/Q_b$, wherein
$Q_a$=Concentration of compound A in parts per million, acting alone, which produced an end point to completely prevent growth of a bacteria,
$Q_b$=Lowest concentration of compound B in parts per million, acting alone, which produced an end point to completely prevent growth of said bacteria,
$Q_A$=Lowest concentration of compound A in parts per million, in the mixture, which produced an end point to completely prevent growth of said bacteria,
$Q_B$=Lowest concentration of compound B in parts per million, in the mixture, which produced an end point to completely prevent growth of said bacteria,
and where the sum of $Q_A/Q_a$ and $Q_B/Q_b$ is less than one, and wherein said bacteria is *Pseudomonas aeruginosa* or *Enterobacter aerogenes*.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A method of controlling the growth of at least one microorganism in or on a product, material, or medium, each of the product, material, or medium susceptible to attack by the at least one microorganism, the method comprising treating the product, material or medium with aqueous solution comprising (a) monochloramine and (b) at least one organic acid, wherein components (a) and (b) are present in a synergistically microbicidally effective combined amount to control the growth of the at least one microorganism, wherein the organic acid is citric acid, formic acid, acetic acid, bromoacetic acid, glycolic acid, propionic acid, glyoxylic acid, gluconic acid, lactic acid, tartaric acid, malonic acid, maleic acid, fumaric acid, pyrrolidone carboxylic acid, sorbic acid, undecenoic acid, undecynoic acid, benzoic acid, hydroxybenzoic acid, salicylic acid, dehydracetic acid, or salts or esters thereof, or any combinations thereof.

2. The method of claim 1, wherein the product, material or medium is fermentable mash or solution, wood pulp or paper, wood chips, lumber, paints, leathers, adhesives, coatings, animal hides, tanning liquor, paper mill liquor, fiberglass, dairy processing, poultry processing, meat packing facilities, meat processing, metalworking fluids, petrochemicals, pharmaceutical formulations, cooling water, recreational water, dyes, clays, mineral slurries, cationic surfactants, formulations with cationic surfactants, influent water, waste water, pasteurizers, retort cookers, cosmetic formulations, toiletry formulations, textiles, geological, drilling lubricants, or agrochemical compositions for crop or seed protection.

3. The method of claim 1, wherein the at least one microorganism is bacteria.

4. The method of claim 1, wherein the product, material or medium is in the form of a solid, a dispersion, an emulsion, a mash, a slurry, or a solution.

5. The method of claim 1, wherein the at least one organic acid is citric acid, or a salt or ester thereof, or any combinations thereof.

6. The method of claim 1, wherein the product, material or medium is fermentable mash or solution.

7. The method of claim 1, wherein the monochloramine is present in the product, material or medium at a concentration of 0.1 ppm to 750 ppm, and the at least one organic acid is present in the product, material or medium at a concentration of 0.1 ppm to 25,000 ppm.

8. The method of claim 1, wherein the monochloramine is present in the product, material or medium at a concentration of 1 ppm to 450 ppm, and the at least one organic acid is present in the product, material or medium at a concentration of 100 ppm to 25,000 ppm.

9. The method of claim 1, wherein the monochloramine is present in the product, material or medium at a concentration of 15 ppm to 150 ppm, and the at least one organic acid is present in the product, material or medium at a concentration of 100 ppm to 25,000 ppm.

10. The method of claim 1, wherein the at least one organic acid is citric acid.

\* \* \* \* \*